United States Patent
Horstmann et al.

(10) Patent No.: US 9,952,234 B2
(45) Date of Patent: Apr. 24, 2018

(54) CALIBRATION METHOD FOR PHOTOMETRY

(71) Applicant: Roche Diagnostics Operations, Inc., Indianapolis, IN (US)

(72) Inventors: Martin Horstmann, Penzberg (DE); Fridl Lang, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 249 days.

(21) Appl. No.: 14/966,804

(22) Filed: Dec. 11, 2015

(65) Prior Publication Data

US 2016/0097785 A1 Apr. 7, 2016

Related U.S. Application Data

(63) Continuation of application No. PCT/EP2014/062015, filed on Jun. 10, 2014.

(30) Foreign Application Priority Data

Jun. 12, 2013 (EP) .................................... 13171586

(51) Int. Cl.
   *G01N 33/96* (2006.01)
   *G01N 21/75* (2006.01)
   (Continued)

(52) U.S. Cl.
   CPC ............ *G01N 33/96* (2013.01); *G01J 1/0295* (2013.01); *G01N 21/274* (2013.01); *G01N 21/75* (2013.01);
   (Continued)

(58) Field of Classification Search
   CPC ...... G01N 33/96; G01N 21/274; G01N 21/75; G01N 33/487; G01J 1/0295
   See application file for complete search history.

(56) References Cited

U.S. PATENT DOCUMENTS

| 4,935,875 A | 6/1990 | Shah et al. |
| 2003/0107738 A1 | 6/2003 | Curtis |

(Continued)

FOREIGN PATENT DOCUMENTS

| EP | 1975623 A2 | 10/2008 |
| EP | 2182364 A2 | 5/2010 |

(Continued)

OTHER PUBLICATIONS

International Search Report dated Sep. 10, 2014 in Application No. PCT/EP2014/062015, 5 pages.

(Continued)

*Primary Examiner* — Krishnan S Menon
*Assistant Examiner* — Dwan A Gerido
(74) *Attorney, Agent, or Firm* — Roche Diagnostics Operations, Inc.

(57) ABSTRACT

A method for determining a physical property of a biological sample. The method comprises the steps of: acquiring a set of preliminary calibration signals of a first lot of a reagent using an automatic analyzer with a first photometry module; acquiring a reference set of signals of the first lot of the reagent using a calibration analyzer with a second photometry module; determining a set of module specific components by subtracting the reference set of signals from the preliminary calibration signals; acquiring a lot specific set of signals of a second lot of the reagent using the second photometry module; determining a lot calibration for the first photometry module using the set of module specific components and the lot specific set of signals; acquiring a measurement signal of the biological sample using the first photometry module and the second lot of the reagent; and determining a physical property of the biological sample using the measurement signal and the lot calibration.

12 Claims, 8 Drawing Sheets

(51) Int. Cl.
*G01N 35/00* (2006.01)
*G01J 1/02* (2006.01)
*G01N 21/27* (2006.01)
*G01N 33/487* (2006.01)

(52) U.S. Cl.
CPC ..... *G01N 33/487* (2013.01); *G01N 35/00693* (2013.01); *G01N 2201/12746* (2013.01); *G01N 2496/00* (2013.01)

(56) References Cited

U.S. PATENT DOCUMENTS

2005/0013736 A1* 1/2005 McKeever ......... G01N 35/0092
422/63
2015/0064795 A1* 3/2015 Ariyoshi .......... G01N 35/00693
436/43

FOREIGN PATENT DOCUMENTS

| WO | 2003/033728 A1 | 4/2003 |
| WO | 2009/029827 A1 | 3/2009 |
| WO | 2011/128893 A2 | 10/2011 |

OTHER PUBLICATIONS

Applied Biosystems 7500/7500 Fast Real-Time PCR Systems System Maintenance, Maintenance Guide, 2013, 109 pages, Chapters 3-4.

* cited by examiner

CALIBRATION METHOD FOR PHOTOMETRY

CROSS-REFERENCE TO RELATED APPLICATIONS

This application is a continuation of International Patent Application No. PCT/EP2014/062015, filed 10 Jun. 2014, which claims the benefit of European Patent Application No. 13171586.4, filed 12 Jun. 2013, the disclosures of which are hereby incorporated by reference in their entirety.

TECHNICAL FIELD

The present disclosure relates generally to the field of medical technology and diagnostics and, in particular, to a method of calibrating photometric measurements of a biological sample with a reagent.

BACKGROUND

One way of analyzing a biological sample is to use photometry. Typically the spectra of scattered light or the transmission at certain wavelengths is measured. Not all molecules have a scattering or transmission spectra which is useful. Solutions containing a reagent may be mixed into the biological sample to alter its spectral properties. Different reagents may be selected which exhibit changes in spectral properties depending upon a physical property such as the concentration of a particular molecule or analyte. In order to make these measurements useful the changes in the spectral properties as a function of the physical property should be calibrated.

SUMMARY

It is against the above background that the embodiments of the present disclosure provide certain unobvious advantages and advancements over the prior art. In particular, the inventors have recognized a need for improvements in calibration methods for photometry.

In accordance with one embodiment of the present disclosure, a method for determining a physical property of a biological sample is provided comprising: acquiring a set of preliminary calibration signals of a first lot of a reagent using an automatic analyzer according to a calibration protocol, wherein the automatic analyzer acquires the preliminary calibration signals using a first photometry module; acquiring a reference set of signals of the first lot of the reagent using a calibration analyzer according to the calibration protocol, wherein the calibration analyzer acquires the reference set of signals using a second photometry module; determining a set of module specific components by subtracting the reference set of signals from the preliminary calibration signals; acquiring a lot specific set of signals of a second lot of the reagent using the second photometry module according to the calibration protocol; determining a lot calibration for the first photometry module using the set of module specific components and the lot specific set of signals; acquiring a measurement signal of the biological sample using the first photometry module and the second lot of the reagent; and determining a physical property of the biological sample using the measurement signal and the lot calibration.

In accordance with another embodiment of the present disclosure, an analysis system comprising an automatic analyzer for analyzing a biological sample is provided, wherein the automatic analyzer comprises: a dispenser for dispensing a reagent into the biological sample, a first photometric module for acquiring a measurement signal of the biological sample, a memory for storing machine executable instructions, and an analyzer controller for controlling the automatic analyzer, and wherein execution of the machine executable instructions cause the analyzer controller to: receive a set of module specific components; receive a lot specific set of signals; determine a lot calibration according to a calibration protocol for a second lot of a reagent using the set of module specific components and the lot specific set of signals; dispense a portion of the second lot of reagent into the biological sample using the dispenser; acquire the measurement signal of the biological sample using the first photometry module; and determine a physical property of the biological sample using the measurement signal and the lot calibration.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The term "analyzer" refers to a device being operable to execute one or multiple analyses on biological samples such as blood, urine, saliva, or other sample types. An analyzer is operable to determine via various chemical, biological, physical, optical or other technical procedures a parameter of the sample or a component thereof, the parameter in the following being referred to as "measurement value." An analyzer is operable to measure said parameter of the sample or of at least one reagent and return the obtained measurement value. The list of possible analysis results returned by the analyzer comprises, without limitation, concentrations of the reagent in the sample, a digital (yes or no) result indicating the existence of the reagent in the sample (corresponding to a concentration above the detection level), optical parameters, DNA or RNA sequences, data obtained from mass spectroscopy of proteins or metabolites, and physical or chemical parameters of various types.

As will be appreciated by one skilled in the art, aspects of the present disclosure may be embodied as a apparatus, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A "computer-readable storage medium" as used herein encompasses any tangible storage medium that may store instructions that are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data that is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory that is directly accessible to a processor. "Computer storage" or "storage" is a further example of a computer-readable storage medium. Computer storage is any non-volatile computer-readable storage medium. In some embodiments computer storage may also be computer memory or vice versa.

A "processor" as used herein encompasses an electronic component that is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code or machine executable instructions may comprise machine executable instructions or a program that causes a processor to perform an aspect of the present disclosure. Computer executable code for carrying out operations for aspects of the present disclosure may be written in any combination of one or more programming languages, including an object oriented programming language such as Java, Smalltalk, C++ or the like, and conventional procedural programming languages, such as the "C" programming language or similar programming languages and compiled into machine executable instructions. In some instances the computer executable code may be in the form of a high level language or in a pre-compiled form and be used in conjunction with an interpreter, which generates the machine executable instructions on the fly.

The machine executable instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart and/or block diagram block or blocks.

A "hardware interface" as used herein encompasses an interface that enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

In accordance with one embodiment of the disclosure, a method of determining a physical property of a biological sample is provided. A physical property as used herein encompasses a property of the biological sample that may be measured. In particular, the physical property may also be an intensive property of the biological sample. This for instance may be the presence or concentration of a particular molecule within the biological sample. A biological sample as used herein encompasses a sample that comprises material generated by a biological system. A biological system may include parts or products of a living organism or chemicals or materials derived or replicated from an organism. For instance, DNA or RNA may be copied by a PCR process although the material is not directly generated by an organism it was derived originally from a biological system or organism.

The method comprises the step of acquiring a set of preliminary calibration signals of a first lot of a reagent using an automatic analyzer according to a calibration protocol. The automatic analyzer acquires the preliminary calibration signals using a first photometry module. Essentially, the set of preliminary calibration signals are a set of photometric measurements. A first lot as used herein is simply a lot of reagent that is referred to as a first lot. The terminology "first lot" is intended to be a label for identifying a particular lot. For instance, the term "first lot" could be replaced with "a first lot of a reagent" instead. An automatic analyzer as used herein encompasses a system for automatically performing a measurement or processing of a biological sample.

A photometry module as used herein encompasses a scientific instrument that illuminates the biological sample with light and then uses a spectrometer to measure the scattered light and/or the light that is transmitted through the biological sample. For instance, a particular reagent may combine with a biological molecule or analyte and may have certain spectroscopic properties that allow the identification of the biological molecule or even the concentration present of the biological molecule within the biological sample. The first and second photometry modules may be, but are not limited to: transmission photometry modules for performing transmission photometric measurements or scattered light photometry modules for measuring scattered light.

The biological sample also encompasses biological material that has been diluted or processed in several ways. For instance, the biological sample may be diluted with a solvent or it may be processed physically such as being placed in a centrifuge or subjected to some other chemical processing. The automatic analyzer may be configured/operable for performing any or all of these operations and also may be configured/operable for adding the reagent to the biological sample automatically.

In another step, the method further comprises the step of acquiring a reference set of signals of the first lot of the reagent using a calibration analyzer according to the calibration protocol. The calibration protocol as used herein encompasses a set of particular measurements that are used to calibrate the photometric measurements of the first lot. For instance, it may involve adding a certain amount of the first lot of the reagent to biological samples that have particular concentrations of biological molecules. The calibration analyzer acquires reference sets of signals using a second photometry module. The calibration analyzer may also be an automatic analyzer or it also may be a manually or partially manually operated analyzer also. The term "calibration analyzer" is intended to be a label to distinguish it from the automatic analyzer previously described. The method is performed using two distinct analyzers.

In accordance with an embodiment of the disclosure, the method further comprises the step of determining a set of module specific components by subtracting the reference set of signals from each of the preliminary calibration signals. The set of preliminary calibration signals and the reference set of signals are both photometric measurements that have been measured according to the calibration protocol. As such, the individual measurements in both the preliminary calibration signals and the reference set of signals can be paired and the reference set of signals are subtracted from the preliminary calibration signals. The calibration protocol may specify measuring the photometric measurement and a particular wavelength band. Intensity or number of counts detected in this wavelength band is the quantity that is processed. Measurements taken by the first photometry module and the second photometry module are largely determined by how the photometry module is constructed. A diffraction grating may be used to break the spectrum into components and then some type of optical detector is used to make a measurement on the light. For instance, a slit could be used to determine the bandwidth of the measurement and a detector such as a photodiode, CCD array, or a photomultiplier tube could be used. In other embodiments the diffraction grating shines the light onto an array of photo detectors and the width of the detector in a specific design of the diffraction grating determines the bandwidth.

The method further comprises the step of acquiring a lot-specific set of signals of a second lot of the reagent using the second photometry module according to the calibration protocol. The term "second lot of the reagent" is a label that is intended to distinguish a second lot or a further lot of the reagent from the first lot of the reagent, which is referred to as the "first lot." The term "lot-specific set of signals" is also intended as a label for the specific photometric measurements that are made on the second lot of the reagent.

The method further comprises the step of determining a lot calibration for the first photometry module using the set of module-specific components and the lot-specific set of signals. In other words, the lot calibration is calculated at least partially using the module specific components and the lot specific set of signals. The method further comprises the step of acquiring a measurement signal of the biological sample using the first photometry module. The method further comprises the step of determining a physical property of the biological sample using the measurement signal and the lot calibration.

This embodiment may be valuable because it may enable the automatic analyzer to use a lot of a reagent without performing a calibration. In this particular method the automatic analyzer and the calibration analyzer first both make photometric measurements according to the calibration protocol on the first lot. This determines a set of module-specific components. The module-specific components are calculated from the photometric measurements on the first lot. Next, a set of photometric measurements referred to as the lot-specific set of signals were measured on a second lot using the second photometry module of the calibration analyzer. For instance, when a manufacturer produces a lot of the reagent the manufacturer could use the calibration analyzer to then acquire the lot-specific set of signals. The lot calibration is then calculated using the lot-specific set of signals and the module-specific components. This enables acquiring the measurement signal and determining the physical property using the first photometry module and the second lot of the reagent.

The measurements needed to provide the valid calibration were done using the calibration analyzer and not the automatic analyzer. For instance, the reagent could be incorporated into a cartridge that contains either the module-specific components or the lot calibration already calculated for the automatic analyzer. The calibration may be performed by a manufacturer or at a different location. The laboratory making the biological sample does not need to perform the calibration protocol in order to use the second lot of the reagent. For instance, it may enable more samples to be performed and increase the throughput of the laboratory.

In another embodiment of the disclosure, the photometry module is configured for measuring the absorbance of the biological sample. The signals are photometric absorbance measurements.

In yet another embodiment of the disclosure, the physical property is the concentration of an analyte.

In still another embodiment of the disclosure, the analyte is any one of the following, but is not limited to: an enzyme, a substrate, a protein, an indicator of drug abuse, an indicator for therapeutic drug monitoring, and other analytes.

In still yet another embodiment of the disclosure, the analyte is a substrate. The analyte may be any one of the following, but is not limited to: Albumin (BCP+BCG), Ammonia, Bicarbonate, Bilirubin-direct, Bilirubin-total, Calcium, Cholesterol, HDL Cholesterol, LDL Cholesterol, Creatinine enz., Creatinine Jaffé, Fructosamine, Glucose, Iron, Lactate, Magnesium, Phosphorus, Total Protein, Total Protein U/CSF, Triglycerides, Triglycerides GB, UIBC, Urea/BUN, and Uric Acid. Reagents for testing for these analytes by measuring the absorbance of light are well known and are commercially available. For example, they may be purchased from Roche Diagnostics, Indianapolis, Ind.

In yet still another embodiment of the disclosure, the analyte is an enzyme. The analyte may be any one of the following, but is not limited to: ACP, ALP, ALT/GPT, Amylase-tot., Amylase-pancr., AST/GOT, Cholinesterase Acetyl, Cholinesterase Butyryl, Cholinesterase Dibucain, CK, CK-MB, GGT, GLDH, HBDH, LDH, and Lipase. Reagents for testing for these analytes by measuring the absorbance of light are well known and are commercially available. For example, they may be purchased from Roche Diagnostics, Indianapolis, Ind.

In yet still another embodiment of the disclosure, the analyte is an electrolyte (ISE). The analyte may be any one of the following, but is not limited to: Chloride, Potassium, and Sodium. Reagents for testing for these analytes by measuring the absorbance of light are well known and are commercially available. For example, they may be purchased from Roche Diagnostics, Indianapolis, Ind.

In accordance with another embodiment of the present disclosure, the analyte is a protein. The analyte may be any one of the following, but is not limited to: α1-Acid Glycoprotein, α1-Antitrypsin, α1-Microglobulin, β-Microglobulin, Albumin (immuno.), APO A1, APO B, ASLO, C3c, C4, Ceruloplasmin, CRP, CRP High Sensitivity, Cystatin C, Ferritin, Haptoglobin, HbA1c (whole blood+hemolysate), Homocysteine, IgA, IgG, IgM, Kappa Light chains, Freelite™ Human Lambda Free, Lambda Light chains, Lipoprotein (a), Myoglobin, Prealbumin, RF, Soluble Transferrin Receptor, and Transferrin. Reagents for testing for these analytes by measuring the absorbance of light are well known and are commercially available. For example, they may be purchased from Roche Diagnostics, Indianapolis, Ind.

In still another embodiment of the disclosure, the analyte is an indicator of drugs of abuse. The analyte may be for testing the abuse of any one of the following drugs, but is not limited to: Amphetamines, Barbiturates, Benzodiazepines, Cannabinoids, Cocaine, LSD, Ethanol, Methadone, Methadone Methabolite (EDDP), Methaqualone, Opiates, Oxycodone, Phencyclidine, and Propoxyphene. Reagents for testing for these analytes by measuring the absorbance of light are well known and are commercially available. For example, they may be purchased from Roche Diagnostics, Indianapolis, Ind.

In yet another embodiment of the disclosure, the analyte is an indicator for therapeutic drug monitoring (TDM). The analyte may be any one of the following, but is not limited to: Acetaminophen, Amikacin, Carbamazepine, Digitoxin, Digoxin, Gentamicin, Lidocaine, Lithium, MPA-T, NAPA, Phenobarbital, Phenytoin, Procainamide, Quinidine, Salicylate, Theophylline, Tobramycin, Valproic Acid, and Vancomycin. Reagents for testing for these analytes by measuring the absorbance of light are well known and are commercially available. For example, they may be purchased from Roche Diagnostics, Indianapolis, Ind.

The analyte may be any one of the following, but is not limited to: D-Dimer and Anti-Thrombin III. Reagents for testing for these analytes by measuring the absorbance of light are well known and are commercially available. For example, they may be purchased from Roche Diagnostics, Indianapolis, Ind.

In yet still another embodiment of the disclosure, the method further comprises the step of acquiring at least one additional calibration signal of the second lot of the reagent using the first photometry module. The method further comprises the step of adjusting the calibration using the at least one additional calibration signal. Some reagents may change over time. For instance, the second lot of the reagent could be manufactured and then the reference set of signals is acquired. The second lot of the reagent then may for instance be shipped to a different location or it may sit unused for a period of time. The measurement of an at least one calibration signal may allow for this change in the reagent over time. For many reagents one or two additional measurements is all that is necessary. Although some calibration measurements are performed this may be less than performing a full calibration. This may be advantageous because it reduces the amount of calibration that needs to be performed before the automatic analyzer uses the second lot of the reagent to determine the physical property of the biological sample.

In another embodiment the measurement of the at least one additional calibration signal and the adjusting of the calibration using the at least one additional calibration signal is repeated after a predetermined duration. The predetermined duration may for instance be preprogrammed into the analyzer controller or may be given as input by an operator. In some embodiments the predetermined duration may be adjusted.

If the reagent which properties change over time is not used up within the predetermined duration, the calibration may have shifted. In this case it may be beneficial to repeat the measurement of the at least one additional calibration signal.

In another embodiment, the step of determining the lot calibration for the first photometry module comprises adding the set of module specific components to the lot specific set of signals.

In another embodiment, the method further comprises the step of calculating a calibration constant by dividing the set of module-specific components by the reference set of signals. Determination of the lot calibration from the first photometry module is determined by multiplying the quantity 1+the calibration constant by the lot-specific set of signals. The first photometry module and the second photometry module are of course optical instruments. In principle the measurements should be identical; however the optical alignment of various components or the efficiency of a particular photo detector may vary from instrument to instrument. For instance this time it may be reflected in different intensities being measured. Measurements in the preliminary calibration signal and the reference set of signals that correspond to each other will be roughly constant when divided by each other. It may provide for a more efficient means of calculating the lot calibration.

In another embodiment, the method further comprises the step of calculating the linear fit between the module-specific components and the reference set of signals. The linear fit comprises a calibration constant and an offset constant wherein the determination of the lot calibration for the first photometry module is determined by adding the offset constant to the product of the calibration constant and the lot-specific set of signals. This embodiment is similar to the previous embodiment except there is some non-linearity in the calibration constant. For instance, photo detectors may have different response curves at different wavelengths of light. Or for different wavelengths the optical alignment may be slightly different. This embodiment is also able to compensate for these differences.

In accordance with another embodiment, the disclosure provides for an analysis system comprising an automatic analyzer for analyzing a biological sample. The automatic analyzer further comprises a dispenser for dispensing the reagent into the biological sample. The automatic analyzer comprises a first photometric module for acquiring the measurement signal of the biological sample. The analysis system comprises a memory for storing machine-executable instructions. The automatic analyzer comprises an analyzer controller for controlling the automatic analyzer. Execution of the machine-executable instructions causes the analyzer controller to receive a set of module-specific components. The set of module-specific components is analogous to the set of module-specific components as described previously with respect to the method. Execution of the machine-executable instructions causes the analyzer controller to further receive a lot-specific set of signals. The lot-specific set of signals is also analogous to the lot-specific set of signals that was previously with respect to the method. There are a variety of ways in which the set of module-specific components and the lot-specific set of signals may be received. For instance, they may both be transmitted to the automatic analyzer via a network connection. The second lot of a reagent may also have a cartridge with a storage device such as an RFID chip or other memory that may store the set of module-specific components or also even the lot-specific set of signals. In some embodiments the set of module-specific components may be stored locally in the memory of the automatic analyzer.

Execution of the machine-executable instructions further cause the analyzer controller to determine a lot calibration according to a calibration protocol for a second lot of a reagent using the set of module-specific components and the lot-specific set of signals. Execution of the machine-executable instructions further cause the analyzer controller to add a reagent from the second lot of reagents to the biological sample using the dispenser. In other words, the machine executable instructions cause the dispenser to dispense a portion of the second lot of reagent into the biological sample. Execution of the machine-executable instructions further cause the analyzer controller to acquire the measurement signal of the biological sample using the photometry module. Execution of the machine-executable instructions further cause the analyzer controller to determine a physical property of the biological sample using the measurement signal and the lot calibration. This embodiment is an implementation of the previously described method of determining a physical property. In this embodiment the steps performed by just the automatic analyzer are described. It is advantageous because it describes components and functions of the apparatus that would be installed within a laboratory to measure the physical property of the biological sample.

In another embodiment, the analysis system further comprises a calibration analyzer with a second photometry module. The analysis system further comprises a calibration controller. Execution of the instructions causes the analyzer controller to acquire the set of preliminary calibration signals of a first lot of a reagent using the automatic analyzer according to a calibration protocol. The automatic analyzer is configured/operable to acquire the preliminary calibration signals using the first photometry module. Execution of the machine-executable instructions further cause the calibration controller to acquire a set of reference set of signals of the first lot of the reagent using the calibration analyzer according to the calibration protocol. The calibration analyzer acquires the reference set of signals using the second photometry module. The analysis system is configured/ operable to determine the set of module-specific components by subtracting the reference set of signals from the preliminary calibration signals.

Execution of the machine-executable instructions cause the calibration controller to acquire the lot-specific set of signals of a second lot of the reagent using the second photometry module according to the calibration protocol. The analysis system is configured/operable to determine the lot calibration for the first photometry module using the set of module-specific components and the lot-specific set of signals. The analyzer controller is configured/operable to receive the calibration correction components from the analysis system. In this embodiment the analysis system comprises both the automatic analyzer and the calibration analyzer as described previously with respect to the method.

In another embodiment, execution of the machine-executable instructions causes the analyzer controller to acquire at least one additional calibration signal of the second lot of the reagent using the first photometry module.

In another embodiment, execution of the machine-executable instructions causes the analyzer controller to acquire at least one additional calibration signal of the second lot of the reagent using the first photometry module. Execution of the machine-executable instructions causes the analyzer controller to adjust the calibration using the at least one additional calibration signal.

In another embodiment, execution of the machine-executable instructions further causes the analyzer controller to repeat the acquisition of the at least one additional calibration signal and the adjusting of the calibration using the at least one additional calibration signal after a predetermined duration.

In another embodiment, the analysis system is further configured/operable for determining the lot calibration for the first photometry module and comprises adding the set of module specific components to the lot specific set of signals. This may be implemented for instance by programming machine-executable instructions into the analyzer controller.

In another embodiment, the analysis system is further configured/operable for calculating the calibration constant by dividing the set of module-specific components by the reference set of signals. The determination of the lot calibration for the first photometry module is determined by multiplying the quantity 1+the calibration constant by the lot-specific set of signals. This may be implemented for instance by programming machine-executable instructions into the analyzer controller.

In another embodiment, the analysis system is further configured/operable for calculating a linear fit between the module-specific components and the reference set of signals. The linear fit comprises a calibration constant and an offset constant. The determination of the lot calibration for the first photometry module is determined by adding the offset constant to the product of the calibration constant and the lot-specific set of signals. This may be implemented for instance by programming machine-executable instructions into the analyzer controller.

In another embodiment, the analysis system further comprises a server for transferring any one of the following to the measurement system via a computer network: the set of calibration correction components, the lot-specific set of signals and combinations thereof.

In another embodiment, the analysis system further comprises a reagent cartridge at least partially filled with the second lot of the reagent. The dispenser is configured/operable for dispensing the reagent from the reagent cartridge.

It is understood that one or more of the aforementioned embodiments of the disclosure may be combined as long as the combined embodiments are not mutually exclusive.

In order that the embodiments of the present disclosure may be more readily understood, reference is made to the following examples, which are intended to illustrate the disclosure, but not limit the scope thereof.

Figure 1:
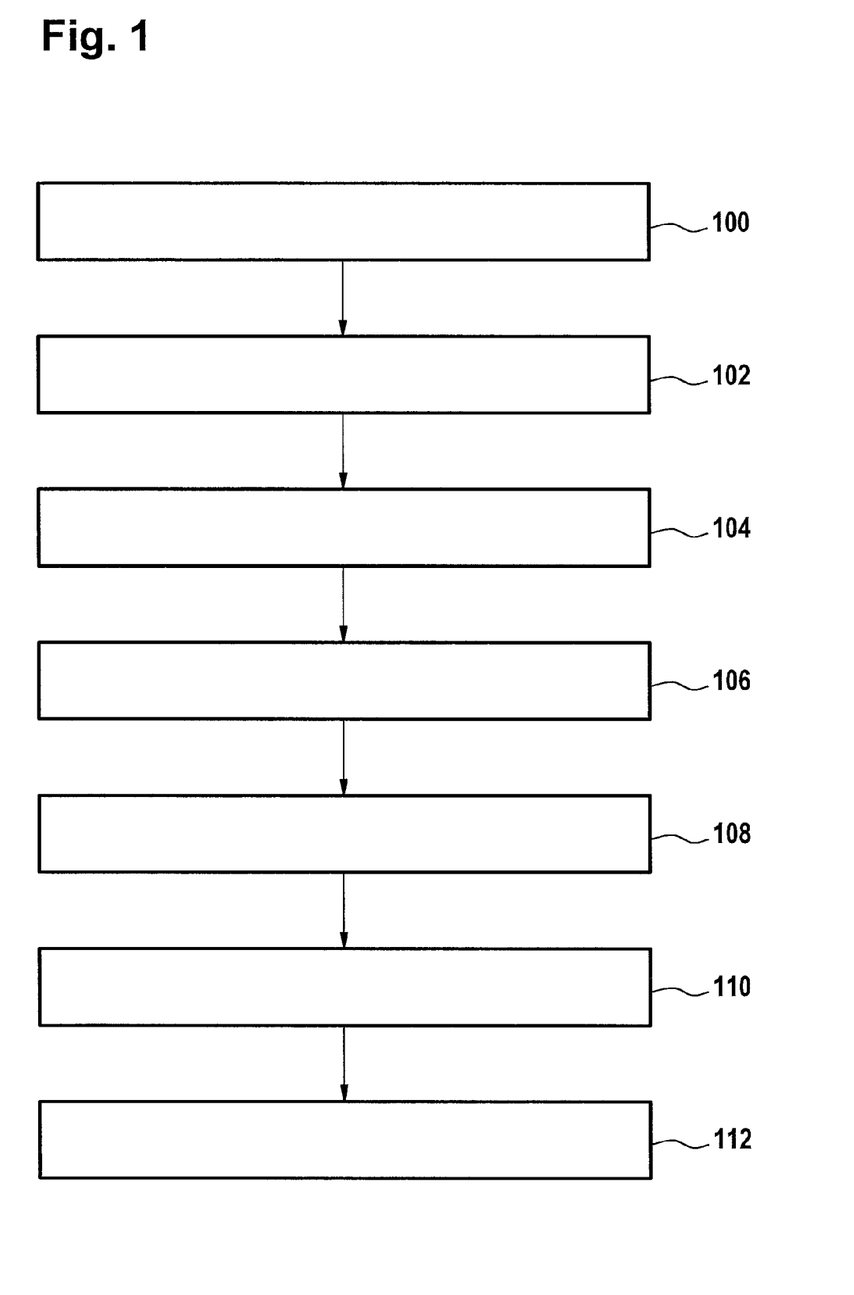
FIG. 1 shows a flow chart that illustrates a method in accordance with an embodiment of the present disclosure.

FIG. 1 shows a flow diagram which illustrates a method of determining a physical property of a biological sample. First, in step 100, a set of preliminary calibration signals is acquired from a first lot of a reagent using an automatic analyzer according to a calibration protocol. The automatic analyzer acquires the preliminary calibration signals using a first photometry module. Next, in step 102, a reference set of signals of the first lot of the reagent is acquired using a calibration analyzer according to the calibration protocol. The calibration analyzer acquires the reference set of signals using a second photometry module. In step 104, a set of module-specific components is determined by subtracting the reference set of signals from the preliminary calibration signals. Next, in step 106, a lot-specific set of signals of a second lot of the reagent is acquired using the second photometry module according to the calibration protocol. Next, in step 108, a lot calibration for the first photometry module is acquired by adding the set of module-specific components to the lot-specific set of signals. Next, in step 110, a measurement signal of the biological sample is acquired using the first photometry module and the second lot of the reagent. Finally, in step 112, a physical property of the biological sample is determined using the measurement signal and the lot calibration.

Figure 2:
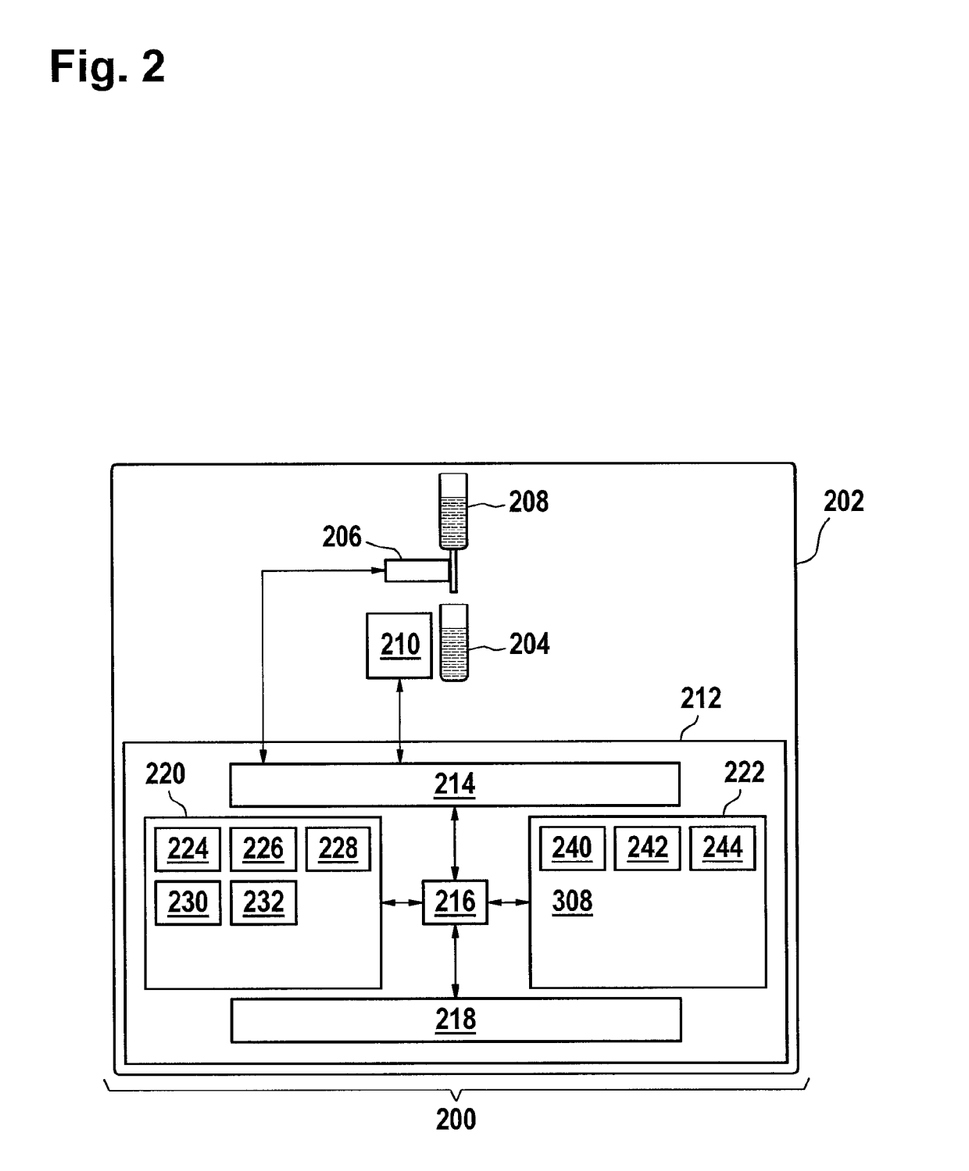
FIG. 2 illustrates an example of an analysis system in accordance with an embodiment of the present disclosure.

FIG. 2 shows an example of an analysis system 200. The analysis system comprises an automatic analyzer 202. The automatic analyzer 202 is configured/operable for analyzing a biological sample 204. There is a dispenser 206 that is configured/operable for dispensing a second lot of reagent 208 into the biological sample 204. The second lot of reagent 208 may for instance be located within a cartridge. Although not shown in this FIG. 2, the automatic analyzer 202 may have an apparatus for positioning multiple biological samples 204 for dispensing the reagent and also for being analyzed by a first photometric module 210. The dispenser 206 and the first photometric module 210 are connected to a hardware interface 214 of a computer system 212. The computer system 212 is one example of an analyzer controller. The computer system 212 further comprises a processor 216, which is in connection with the hardware interface 214, a network interface 218, computer storage 220 and computer memory 222. The computer storage 220 is shown as containing a set of module-specific components 224. The computer storage is further shown as containing a lot-specific set of signals 226. The computer storage 220 is further shown as containing a lot calibration. The computer storage 220 is further shown as containing a measurement signal 230. The computer storage 220 is further shown as containing a value of a physical property. The value representing the physical property 232 can be considered to be a measurement of the physical property of the biological sample 204. In some embodiments only the lot calibration 228 is received. In other examples the set of module-specific components 224, and the lot-specific set of signals are received. These, for instance, may be received by the network interface 218.

The computer memory 222 is shown as containing a control module 240. The control module 240 contains computer-executable code that enables the processor 216 to control the operation and function of the automatic analyzer 202. For instance, this may control the dispenser 206 to dispense the reagent into the biological sample 204. The control module 240 may also contain instructions that cause the processor 216 to control the first photometry module 210 to acquire the measurement signal 230. The computer storage 222 is further shown as containing a calibration calculation module 242. The calibration calculation module 242 is an optional module present in some examples, which contains code that enables the processor 216 to calculate the lot calibration 228 using the set of module-specific components 224 and the lot-specific set of signals 226. The computer memory 222 is further shown as containing a measurement calculation module 244, which enables the processor 216 to calculate the value representing the physical property 232 from the measurement signal 230 and the lot calibration 228.

Figure 3:
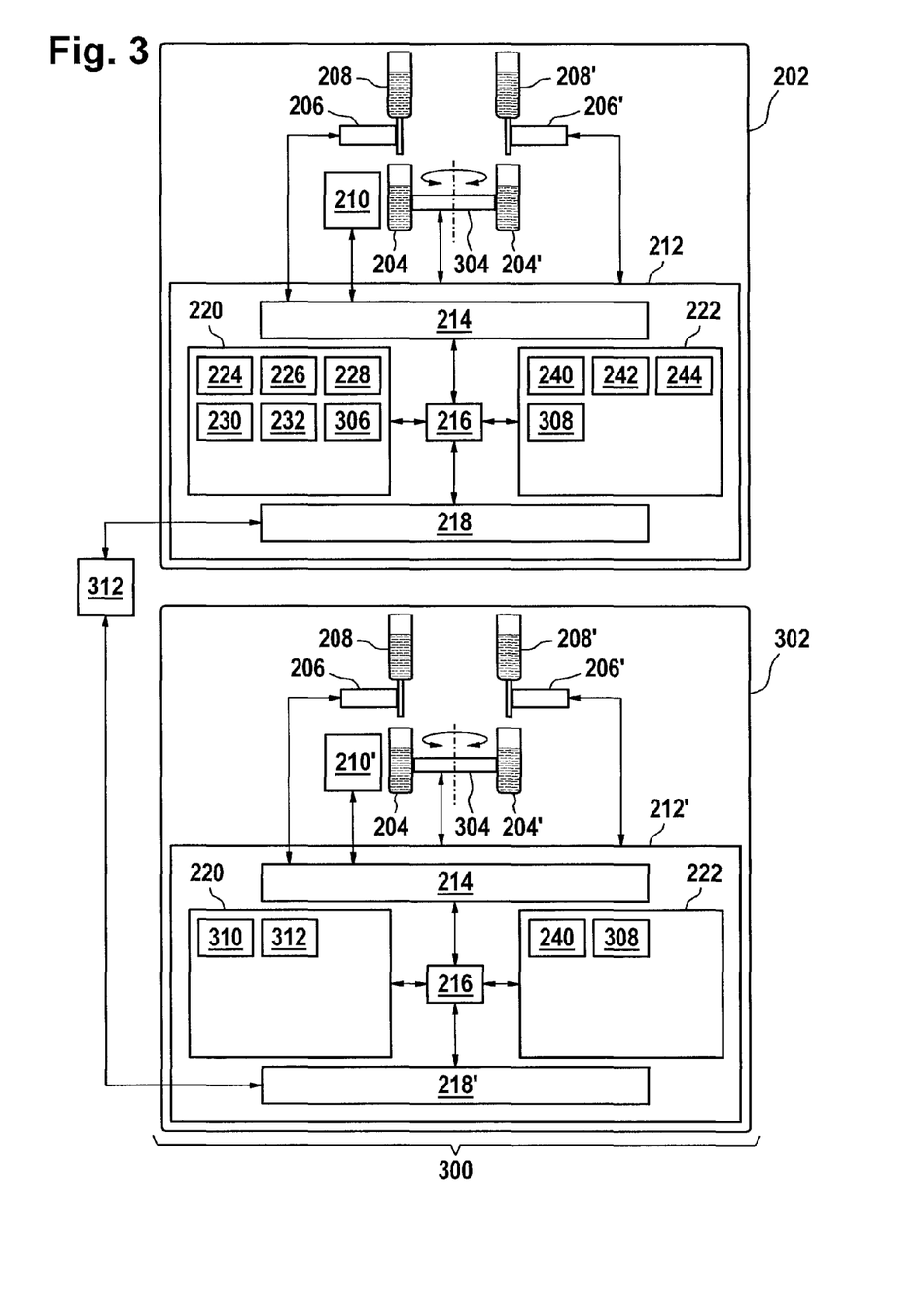
FIG. 3 illustrates a further example of an analysis system in accordance with an embodiment of the present disclosure.

FIG. 3 shows a further example of an analysis system 300. The analysis system 300 comprises an automatic analyzer 202 similar to that shown in FIG. 2, a calibration analyzer 302, and a server 312. The automatic analyzer 202 additionally contains a sample movement system 304 that is able to move multiple biological samples 204, 204' into position for measurement of a first photometric module 210 and/or between different dispensers 206, 206'. The automatic analyzer 202 may comprise multiple dispensers 206, 206'. In this example there are two dispensers 206, 206' for dispensing a second lot of the reagent 208 and a first lot of the reagent 208'. In practical use the first lot 208 would be used for measurements in the automatic analyzer 202 at a point in the future when the second lot of the reagent 208 is used. Both are shown in this FIG. 3 to illustrate the measurements taken on the second lot of the reagent 208 and the first lot of the reagent 208'.

The computer storage 220 is additionally shown as containing preliminary calibration signals 306. The preliminary calibration signals 306 were measured using the first lot of the reagent 208' according to a calibration protocol 308. The computer memory is additionally shown as containing a calibration protocol module 308, which enables the processor 216 to follow a calibration protocol. This would likely involve measuring biological samples with known concentrations of a particular molecule that reacts with the reagent. The calibration analyzer 302 is shown as having a configuration nearly identical to the automatic analyzer 202 shown in FIG. 3. The computer 212' contains many of the same components and has the same functionality as the computer 212. The calibration analyzer 302 comprises a computer 212' that functions as the calibration controller. The computer storage 220 of the calibration analyzer 302 contains a reference set of signals 310 measured from the first lot of the reagent 208' and a lot-specific set of signals 312 measured from the second lot of the reagent 208 according to the calibration protocol 308. The set of module-specific components 24 can be determined by subtracting the reference set of signals 310 from the preliminary calibration signals 306. This could be performed by the automatic analyzer 202, the calibration analyzer 302, or the server 312. There is a server 312 that serves to exchange data between the automatic analyzer 202 and the calibration analyzer 302.

Figure 4:
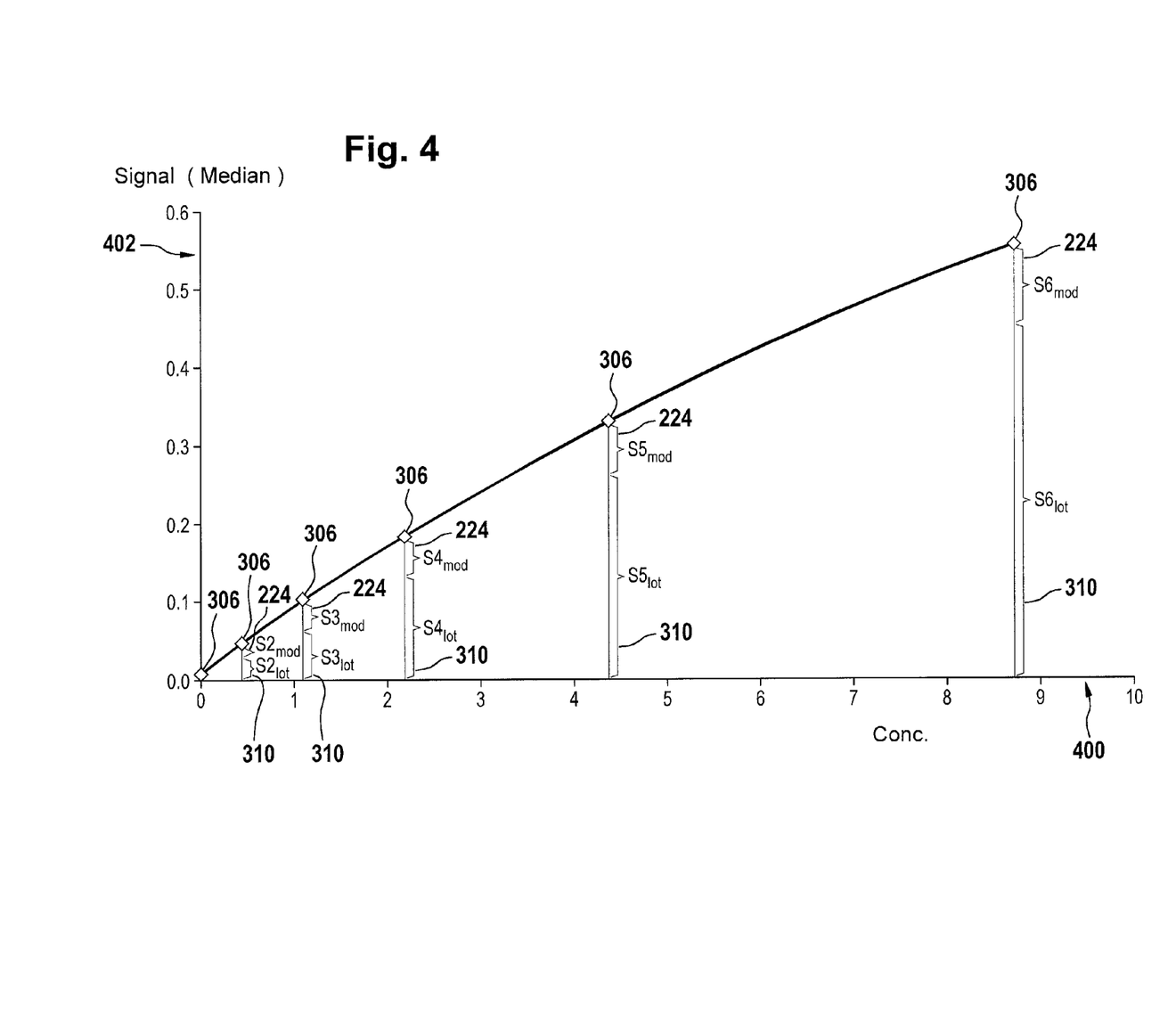
FIG. 4 illustrates calculating the set of module specific components in accordance with an embodiment of the present disclosure.

FIG. 4 shows an example of molecule concentration versus a measurement signal 402 for a calibration protocol. The points labeled 306 correspond to the preliminary calibration signals measured using the automatic analyzer. Each of these signals 306 can be broken into two components. The components correspond to the reference set of signals and the module-specific components 224. The module-specific components 224 are calculated by subtracting each of the preliminary calibration signals 306 by its corresponding reference set of signals.

The observed signals can be abbreviated $S_{obs}$, and are the points 306 in FIG. 4. The six points 306 can be represented by the variables $Sx_{obs}$, where x is an index variable. The lot specific components 310 can be represented as $Sx_{lot}$, where x is again an index variable. The module specific components can be represented as $Sx_{mod}$, where x is again an index variable.

The relationship shown in FIG. 4 can be expressed as:

$$Sx_{obs} = Sx_{lot} + Sx_{mod}.$$

In some cases the ratio $Sx_{obs}/Sx_{lot} = \text{const}_{mod}$ is constant for each photometric module, in this case $S_{obs}$ can be expressed as:

$$Sx_{obs} = Sx_{lot} + Sx_{lot} * \text{const}_{mod}.$$

An example of a workflow outlined for applying the method is first to derive module-specific values from reagents with known lot values. Next, in step 2, lot-specific values of photometric absorbencies are provided as analytical files, for example from a server. Next, in step 3, for new or following first lots the expected absorbency values can be calculated. Next, in step 4, calculated signal values are used for calculation of the curve parameters as a lot calibration. It may be necessary to use water for S0 or zero concentration determination. Next, in step 5, reagents with on-board timeout or cassette calibration should use system water and an S1 calibrator in case of non-linear calibration curves, also 1 or 2 point updates may be considered for on-board recalibration. Next, in step 6, there are many different cases which examples of the method can be applied to: the analyzer installation, a new lot of reagent being used by the automatic analyzer, and new first lot being used at the calibration analyzer are shown in FIG. 5.

Figure 5:
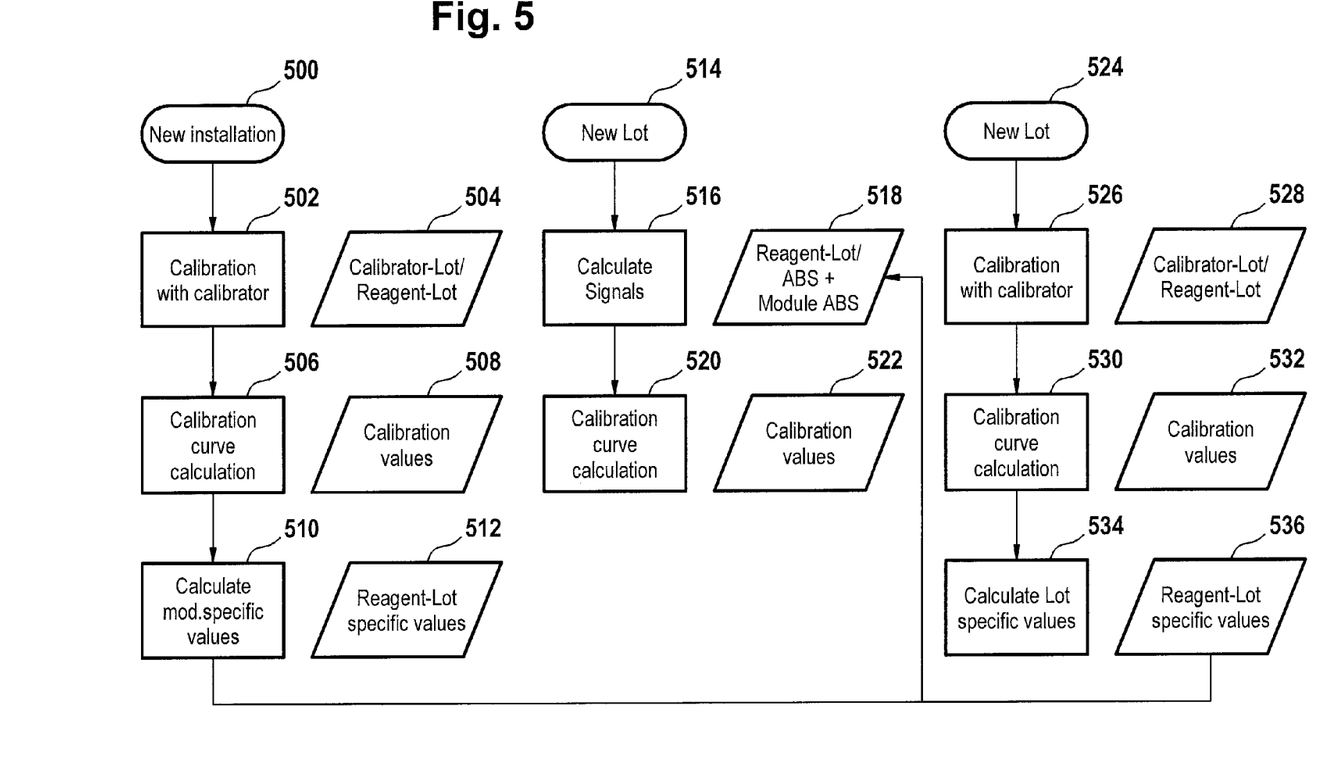
FIG. 5 shows a flow chart that illustrates a further method in accordance with an embodiment of the present disclosure.

FIG. 5 shows three different flowcharts. The first flowchart begins with step 500 wherein a new photometer is installed at a laboratory. Next, in step 502, a calibration is performed with a calibrator. This makes measurements on the calibrator lot and first lot 504. Next, in step 506, a calibration curve calculation is performed. This is done using calibration values 508. Next, in step 510, module-specific values 510 are calculated using the first lot-specific values 512. The analyzer installation corresponds to step 500 and step 512.

The second flowchart begins with step 514, wherein a new lot of reagent at a customer site is started. Next, in step 516, signal values are calculated. This is done using the first lot in addition to the ABS+the module ABS 518. Finally, in step 520, calibration curve calculation is done using calibration values 522.

The third flowchart begins at step 524, which shows an example of a new reagent lot being processed by a calibration analyzer. First, in step 526, a calibration is performed with the calibrator for the first lot and the second lot 528. Next, in step 530, a calibration curve calculation is performed using calibration value 532. And, finally, lot-specific values are calculated in step 534, using the first lot and specific values 536.

Figure 6:
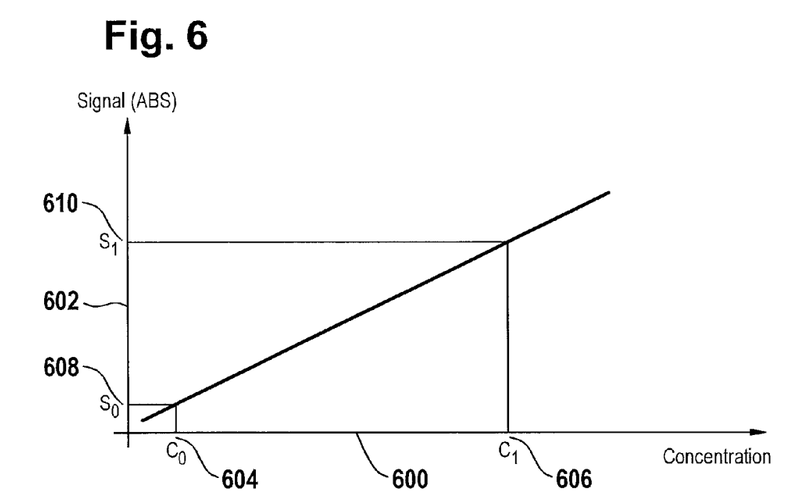
FIG. 6 shows an example of a simple linear two point calibration in accordance with an embodiment of the present disclosure.

FIG. 6 shows an example of a simple linear two point calibration in accordance with an embodiment of the present disclosure. The X-axis 600 is the concentration and the Y-axis 602 is the measured signal. This figure is used to illustrate the case where the lot calibration for the first photometry module is determined by adding the set of module specific components to the lot specific set of signals.

Concentration $C_0$ is labeled 604. Concentration $C_1$ is labeled 606. Signal $S_0$ 608 is the signal that corresponds to Concentration $C_0$ 604. Signal $S_1$ 610 is the signal that corresponds to concentration $C_1$ 616.

In this example, it is assumed that a simple linear two point calibration where $S_0$ 608 is the signal with concentration $C_0$ 604 and $S_1$ is the signal of concentration $C_1$ 606. Then the calibration curve can be expressed as linear regression of ($C_0/S_0$ $C_1/S_1$).

The signals can also be expressed as $S_0 = S_{(mod)} + S_{0(lot)}$ and $S_1 = S_{(mod)} + S_{1(lot)}$. $C_0$ may be 0 and in this case $S_0$ may be derived from the second reagent lot—a signal measured for just the reagent or simply a blank signal.

Another way of performing the calibration is to calculate a calibration constant by dividing the set of module specific components by the reference set of signals. The determination of the lot calibration for the first photometry module is then determined by multiplying the quantity 1 plus the calibration constant by the lot specific set of signals. This technique is in general illustrated by FIG. 4 and the table below.

In the following example, a non-linear calibration curve is made using six calibration points to build the calibration curve. The example is illustrated with the following table.

| Concentration | Signal(ABS) | S (from second module) | Factor |
|---|---|---|---|
| $C_0$ | $S_0 = S_{0\ (lot)}*(1 + x)$ | $S_{0\ (lot)}$ | x |
| $C_1$ | $S_1 = S_{1\ (lot)}*(1 + x)$ | $S_{1(lot)}$ | x |
| $C_2$ | $S_2 = S_{2\ (lot)}*(1 + x)$ | $S_{2\ (lot)}$ | x |
| $C_3$ | $S_3 = S_{3\ (lot)}*(1 + x)$ | $S_{3\ (lot)}$ | x |
| $C_4$ | $S_4 = S_{4\ (lot)}*(1 + x)$ | $S_{4\ (lot)}$ | x |
| $C_5$ | $S_5 = S_{5\ (lot)}*(1 + x)$ | $S_{5\ (lot)}$ | x |

In this table the Factor "x" is the calibration constant and the values of S with the (lot) subscript are the lot specific set of signals. The module specific factor in this case "x" can be derived by least square regression during initial setup of the module. The lot specific set of signals are labeled 310 in FIG. 4.

The effectiveness of this method of calibrating is demonstrated with a calibration for measuring the concentration of IgA in human serum.

Figure 7:
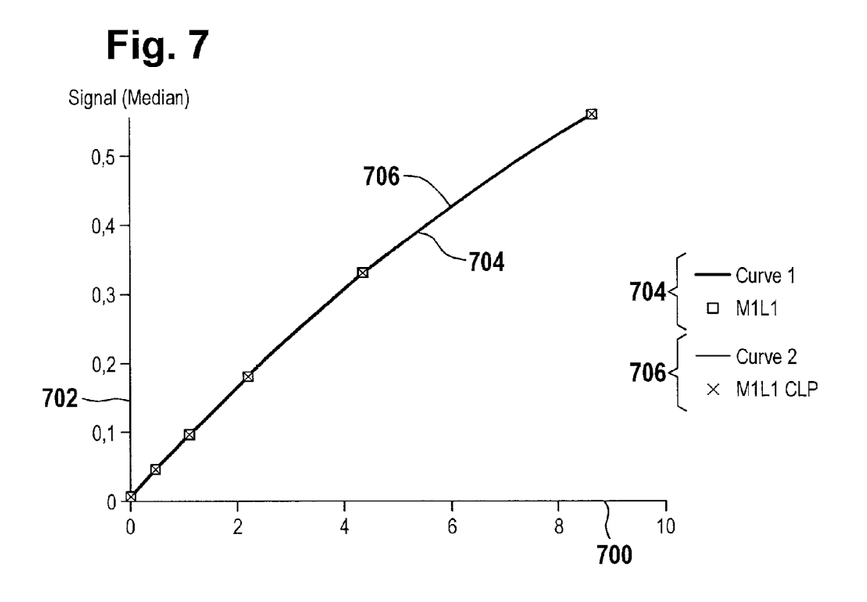
FIG. 7 illustrates two calibration curves for the Roche IGA-2 reagent used on a Roche cobas c system, in accordance with an embodiment of the present disclosure.

FIG. 7 illustrates two calibration curves for the Roche IGA-2 reagent used on a Roche cobas c system. This reagent is a test for IgA in human serum and uses two working solutions. A TRIS buffer is used for the first solution and Anti-human IgA antibody (goat) is used for the second solution. The X-axis 700 shows the concentration in g/L, the Y-axis 702 shows the measured signal for a bi-chromatic calculation. The difference of absorption at two different wavelengths is used. In this particular case, for IGA-1, the signal is the difference of the absorption at 340 nm minus the absorption at 700 nm. There are two calibration curves shown. One using a standard calibration 704, which was performed on the instrument making the measurements. The second calibration curve 706 was performed using a calibration as is illustrated in FIG. 4 and the above table. Comparing the two curves 704, 706 it can be seen that the difference is not visible in the plot.

Figure 8:
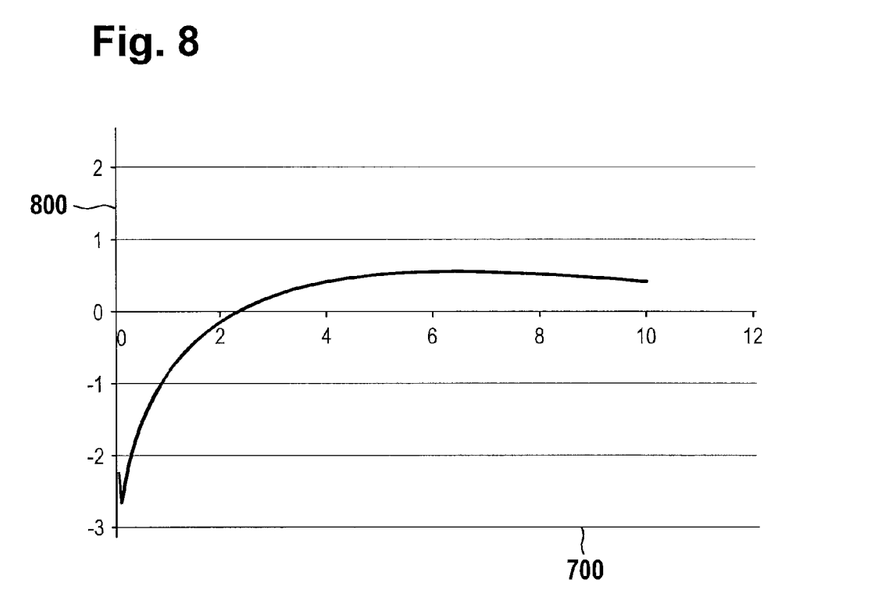
FIG. 8 plots the percent difference between the calibration curves in FIG. 7.

FIG. 8 is used to illustrate the difference between the curves 704 and 706 in FIG. 7. The X-axis 700 is the concentration and Y-axis 800 shows the difference between curves 706 and 704 in terms of the percent change. The percent error or change is shown to be below 1 percent for all but low concentrations.

Figure 9:
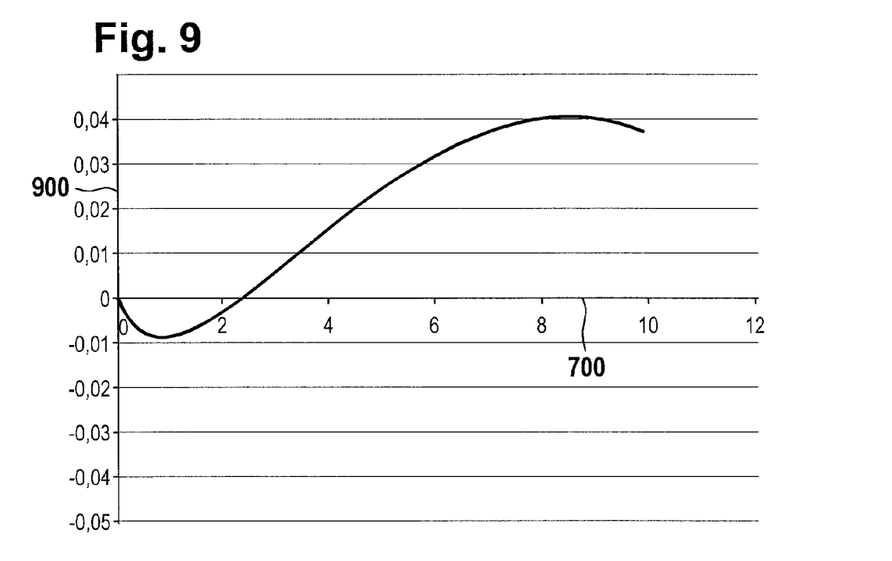
FIG. 9 plots the difference between calibration curves in FIG. 7 in absolute terms.

FIG. 9 shows the difference between curves 704 and 706 in absolute terms. The X-axis 700 is the concentration and the Y-axis 900 is the measured signal. Again, 1 corresponds to the entire signal be absorbed as is the axis 702 in FIG. 7. From this plot it can be seen that at low concentrations the difference or error between the two calibrations is small. FIGS. 8 and 9 together illustrate the effectiveness of the calibration.

The table below is used to illustrate an alternative where a linear fit is calculated between the module specific components and the reference set of signals. The linear fit comprises a calibration constant and an offset constant. The determination of the lot calibration for the first photometry module is then determined by adding the offset constant to the product of the calibration constant and the lot specific set of signals.

As with the previous example, the non-linear calibration curves is built up using six calibration points.

| Concentration | Signal(ABS) | S (from second module) | Factor | constant |
|---|---|---|---|---|
| $C_0$ | $S_0 = S_{0\ (lot)}*(1 + x) + b\ S_{0\ (lot)}$ | | a | b |
| $C_1$ | $S_1 = S_{1\ (lot)}*(1 + x) + b\ S_{1(lot)}$ | | a | b |
| $C_2$ | $S_2 = S_{2\ (lot)}*(1 + x) + b\ S_{2\ (lot)}$ | | a | b |
| $C_3$ | $S_3 = S_{3\ (lot)}*(1 + x) + b\ S_{3\ (lot)}$ | | a | b |
| $C_4$ | $S_4 = S_{4\ (lot)}*(1 + x) + b\ S_{4\ (lot)}$ | | a | b |
| $C_5$ | $S_5 = S_{5\ (lot)}*(1 + x) + b\ S_{5\ (lot)}$ | | a | b |

In this table the Factor "x" is the calibration constant, the values of S with the (lot) subscript are the lot specific set of signals, and b is the offset constant. The module specific factors "x" and "b" can be derived by least square regression during initial setup of the module.

Figure 10:
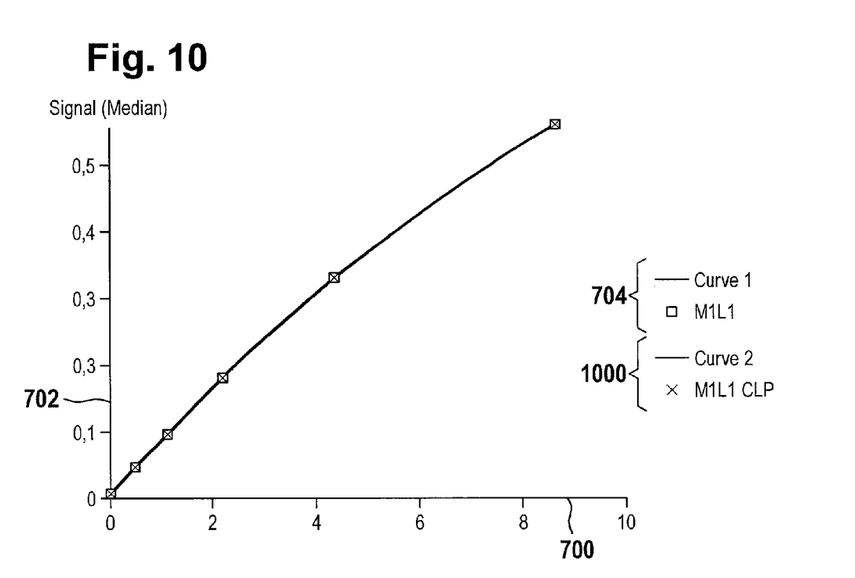
FIG. 10 illustrates two alternative calibration curves for the Roche IGA-2 reagent used on a Roche cobas c system using the same data as was used in FIG. 7.

FIG. 10 illustrates two calibration curves for the Roche IGA-2 reagent used on a Roche cobas c system using the same data as was used in FIG. 7. There are also two calibration curves shown in FIG. 10. One curve uses the standard calibration 704, which was performed on the instrument making the measurements. The second calibration curve 1000 was performed using a calibration as is illustrated in the above table with both the calibration constant and the offset constant. Comparing the two curves 704, 1000 it can be seen that the difference is not visible in the plot.

Figure 11:
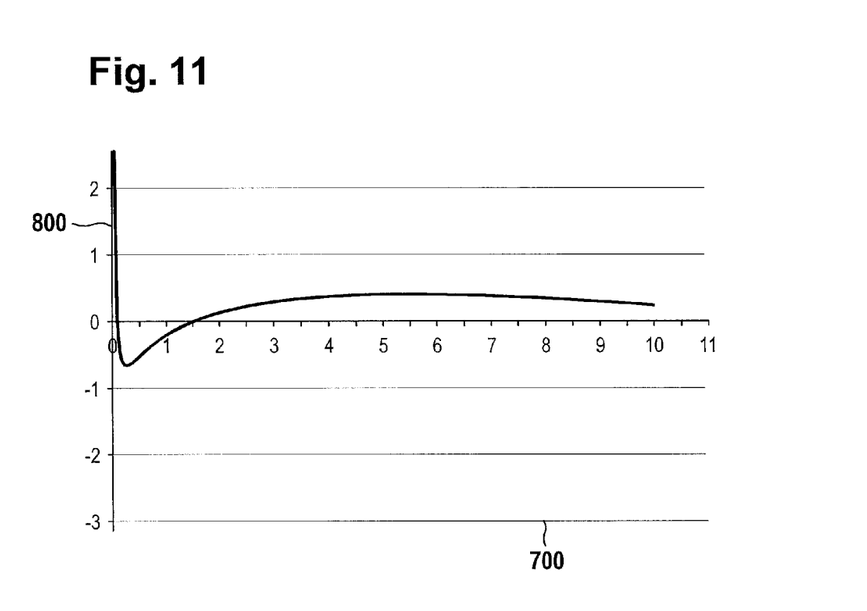
FIG. 11 plots the percent difference between the calibration curves in FIG. 10.

FIG. 11 is used to illustrate the difference between the curves 704 and 1000 in FIG. 10. The X-axis 700 is the concentration and Y-axis 800 shows the difference between curves 1000 and 704 in terms of the percent change. The percent error or change is shown to be reduced when compared to the percentage error shown in FIG. 8.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents. Numbered embodiments are presented below.

LIST OF REFERENCE NUMERALS 200 analysis system
202 automatic analyzer
204 biological sample
206 dispenser
206' dispenser
208 second lot of reagent
208' first lot of reagent
210 first photometric module
210' second photometric module
212 computer
212' computer
214 hardware interface
216 processor
218 network interface
218' network interface
220 computer storage
222 computer memory
224 set of module specific components
226 lot specific set of signals
228 lot calibration
230 measurement signal
232 value representing a physical property
240 control module
242 calibration calculation module
244 measurement calculation module
300 analysis system
302 calibration analyzer
304 sample movement system
306 preliminary calibration signals
308 calibration protocol module
310 reference set of signals
312 lot specific set of signals
314 server
400 concentration
402 signal
600 X-axis (concentration)
602 Y-axis (signal)
604 concentration of analyte
606 concentration of analyte
608 signal
610 signal
700 Y-axis (signal)
704 calibration curve
706 calibration curve
800 Y-axis (percent change)
900 Y-axis (absolute difference)
1000 calibration curve

What is claimed is:

1. A method for determining a physical property of a biological sample comprising:
acquiring a set of preliminary calibration signals of a first lot of a reagent using an automatic analyzer according to a calibration protocol, wherein the automatic analyzer acquires the preliminary calibration signals using a first photometry module;
acquiring a reference set of signals of the first lot of the reagent using a calibration analyzer according to the calibration protocol, wherein the calibration analyzer acquires the reference set of signals using a second photometry module;
determining a set of module specific components by subtracting the reference set of signals from the preliminary calibration signals;
acquiring a lot specific set of signals of a second lot of the reagent using the second photometry module according to the calibration protocol;
determining a lot calibration for the first photometry module using the set of module specific components and the lot specific set of signals;
acquiring a measurement signal of the biological sample using the first photometry module and the second lot of the reagent; and
determining a physical property of the biological sample using the measurement signal and the lot calibration.

2. The method of claim 1 further comprising:
acquiring at least one additional calibration signal of the second lot of reagent using the first photometry module; and
adjusting the calibration using the at least one additional calibration signal.

3. The method of claim 2, wherein the measurement of the at least one additional calibration signal and the adjusting of the calibration using the at least one additional calibration signal is repeated after a predetermined duration.

4. The method of claim 1, wherein the step of determining the lot calibration for the first photometry module comprises adding the set of module specific components to the lot specific set of signals.

5. The method of claim 1 further comprising calculating a calibration constant by dividing the set of module specific components by the reference set of signals, wherein the determination of the lot calibration for the first photometry module is determined by multiplying the quantity 1 plus the calibration constant by the lot specific set of signals.

6. The method of claim 1 further comprising calculating a linear fit between the module specific components and the reference set of signals, wherein the linear fit comprises a calibration constant and an offset constant, and wherein the determination of the lot calibration for the first photometry module is determined by adding the offset constant to the product of the calibration constant and the lot specific set of signals.

7. The method of claim 1, wherein the photometry module is configured for measuring the absorbance of the biological sample.

8. The method of claim 7, wherein the preliminary calibration signals, the reference set of signals, the lot specific set of signals, and the measurement signal are photometric absorbance measurements.

9. The method of claim 1, wherein the physical property is the concentration of an analyte.

10. The method of claim 9, wherein the analyte is any one of the following: an enzyme, a substrate, a protein, an indicator of drugs of abuse, and an indicator for monitoring therapeutic drug use.

11. The method of claim 9, wherein the analyte is any one of the following: Albumin (BCP+BCG), Ammonia, Bicarbonate, Bilirubin-direct, Bilirubin-total, Calcium, Cholesterol, HDL Cholesterol, LDL Cholesterol, Creatinine enz., Creatinine Jaffé, Fructosamine, Glucose, Iron, Lactate, Magnesium, Phosphorus, Total Protein, Total Protein U/CSF, Triglycerides, Triglycerides GB, UIBC, Urea/BUN, Uric Acid, ACP, ALP, ALT/GPT, Amylase-tot., Amylase-pancr., AST/GOT, Cholinesterase Acetyl, Cholinesterase Butyryl, Cholinesterase Dibucain, CK, CK-MB, GGT, GLDH, HBDH, LDH, Lipase, Chloride, Potassium, Sodium, α1-Acid Glycoprotein, α1-Antitrypsin, α1-Microglobulin, β-Microglobulin, Albumin (immuno.), APO A1, APO B, ASLO, C3c, C4, Ceruloplasmin, CRP, CRP High Sensitivity, Cystatin C, Ferritin, Haptoglobin, HbA1c (whole blood+ hemolysate), Homocysteine, IgA, IgG, IgM, Kappa Light chains, Freelite™ Human Lambda Free, Lambda Light chains, Lipoprotein (a), Myoglobin, Prealbumin, RF, Soluble Transferrin Receptor, Transferrin, D-Dimer, and Anti-Thrombin III.

12. The method of claim 9, wherein the analyte may be for testing the usage of any one of the following drugs: Amphetamines, Barbiturates, Benzodiazepines, Cannabinoids, Cocaine, LSD, Ethanol, Methadone, Methadone Methabolite (EDDP), Methaqualone, Opiates, Oxycodone, Phencyclidine, Propoxyphene, Acetaminophen, Amikacin, Carbamazepine, Digitoxin, Digoxin, Gentamicin, Lidocaine, Lithium, MPA-T, NAPA, Phenobarbital, Phenytoin, Procainamide, Quinidine, Salicylate, Theophylline, Tobramycin, Valproic Acid, and Vancomycin.

* * * * *